US006350780B1

(12) United States Patent
Garst et al.

(10) Patent No.: US 6,350,780 B1
(45) Date of Patent: Feb. 26, 2002

(54) METHODS AND COMPOSITIONS FOR DRUG DELIVERY

(75) Inventors: Michael E. Garst, Newport Beach; Joseph S. Adorante, Irvine, both of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/286,147

(22) Filed: Apr. 5, 1999

Related U.S. Application Data (63) Continuation-in-part of application No. 08/260,648, filed on Jul. 28, 1995, now Pat. No. 5,891,911.

(51) Int. Cl.[7] .................................................. A61K 31/235
(52) U.S. Cl. ....................................... 514/532; 514/912
(58) Field of Search .................................. 514/532, 912

(56) References Cited

U.S. PATENT DOCUMENTS

| | | |
|---|---|---|
| 3,467,756 A | 9/1969 | Stone |
| 4,197,301 A | 4/1980 | Smith et al. |
| 4,565,821 A | 1/1986 | Chiou |
| 4,886,815 A | 12/1989 | Schachar |
| 5,066,664 A | 11/1991 | Poli et al. |
| 5,091,528 A | 2/1992 | Gluchowski |
| 5,260,059 A | 11/1993 | Acott et al. |
| 5,380,303 A | 1/1995 | Holly et al. |
| 5,891,911 A * | 4/1999 | Adorante et al. |

FOREIGN PATENT DOCUMENTS

| | | |
|---|---|---|
| EP | 0 464 727 | 1/1992 |
| WO | WO 94/08573 | 4/1994 |
| WO | WO 94/22483 | * 10/1994 |
| WO | WO 95/34302 | * 12/1995 |
| WO | WO 99/16741 | * 4/1999 |

OTHER PUBLICATIONS

Hasan et al, "Cationic and Uncharged Substrates and Reversible Inhibitors in Hydrolysis by Acetylcholinesterase (EC 3.1.1.7)", The Journal of Biological Chemistry, vol. 256, No. 15, Issue of Aug. 10, pp. 7781–7785, 1981.

Hasan et al, "Hydroylsis by Acetylcholinesterase", The Journal of Biological Chemistry, vol. 255, No. 9, Issue of May 10, pp. 3898–3904, 1980.

Cohen et al, "1–Bromopinacolone, an Active Site–directed Covalent Inhibitor for Acetylcholinesterase*" The Journal of Biological Chemistry, vol. 257, No. 23, Issue of Dec. 10, pp. 14087–14092, 1982.

Schlaepfer et al, Neurochemical Research, vol. 6, No. 3, 1981, Calcium–Mediated Breakdown of Glial Filaments and Neurofilaments in Rat Optic Nerve and Spinal Cord, pp. 243–255.

Tymianski et al, Neuron, vol. 11, Aug. 1993, Cell–Permanent Ca2+ Chelators Reduce Early Excitotoxic and Ischemic Neuronal Injury In Vitro and In Vivo, pp. 221–235.

Robert E. Kennedy, Transactions of the Americal Opthalmological Society, vol. LXXII, 1974, Further Observations On Atypical Band Keratopathy In Glaucoma Patients, pp. 107–122.

Thomas J. Zimmerman, Annals of Ophthalmology vol. 11, No. 5, May 1979, Medical Trabeculocanalotomy In Monkeys With Cytochalasin B or EDTA, pp. 795–796.

Anders Bill, Upsala Journal of Medical Sciences, vol. 85, No. 3, 1980, Effects of Na2EDTA and Alpha–Chymotrypsin On Aqueous Humor Outflow conductance in Monkey Eyes.

Bill et al, Investigative Opthalmology & Visual Science, vol. 19/5, May 1980, Effects of intrcameral Na2EDTA and EGTA on Aqueous Outflow routes in the Monkey Eye, pp. 492–504.

Richard P. Haughland, Molecular Probes; Handbook of Fluorescent Probes and Research Chemicals, 1992–1994; Set 20; Calcium Indicators, Chelators and Ionophores, pp. 113–120.

* cited by examiner

*Primary Examiner*—Zohreh Fay
(74) *Attorney, Agent, or Firm*—Carlos A. Fisher; Martin A. Voet; Robert J. Baran (57) ABSTRACT

Pharmaceutical compositions and a method are disclosed for treating glaucoma and/or ocular hypertension in the mammalian eye by administering to the mammalian eye the pharmaceutical composition of the invention which contains as the active ingredient one or more compounds having calcium chelating activity. Examples of calcium chelating agents utilized in the pharmaceutical composition and method of treatment are:

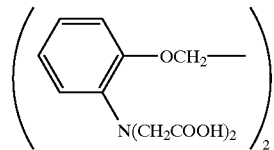

and lower alkyl and alkoxyalkyl esters thereof. Also disclosed are methods and compositions for delivering a drug within the cytoplasm of a cell having cell surface acetylcholinesterase or acetylcholinesterase receptors, wherein the compositions comprise an apolar prodrug joined to an acetylcholine ester or psuedoacetylcholine group.

12 Claims, 2 Drawing Sheets

METHODS AND COMPOSITIONS FOR DRUG DELIVERY

This application is a continuation-in-part of Ser. No. 08/260,648 filed Jul. 28, 1995, now U.S. Pat. No. 5,891,911.

FIELD OF THE INVENTION

The present invention is directed to pharmaceutical compositions, and primarily to topically applied ophthalmic compositions comprising as the active ingredient one or more compounds having the ability to chelate calcium ions, e.g. intracellular calcium ions. The pharmaceutical compositions are useful for reducing intraocular pressure in animals of the mammalian species. In another aspect, the present invention is directed to administering such formulations and compositions to animals of the mammalian species (including humans) for reducing intraocular pressure in the eye. Yet another aspect of the invention concerns methods of delivering a drug to a cell by joining the drug to an acetylcholine or psuedoacetylcholine group, thereby targeting cells containing cell surface acetylcholinesterase or acetylcholine receptors. The drug preferably contains carboxylic acid groups that are neutralized using alkyl ester blocking groups to form a prodrug. Following cell surface binding, the prodrug is able to pass through the cell membrane whereupon the neutralizing blocking groups are removed through the action of intracellular enzymes to release the drug. Preferred prodrugs include acetoxymethyl esters of BAPTA.

BRIEF DESCRIPTION OF THE PRIOR ART

Glaucoma is an optical neuropathy associated with elevated intraocular pressures which are too high for normal function of the eye, and results in irreversible loss of visual function. It is estimated in medical science that glaucoma afflicts approximately 2 percent of the population over the age of forty years, and is therefore a serious health problem. Ocular hypertension, i.e. the condition of elevated intraocular pressure, which has not yet caused irreversible damage, is believed to represent the earliest phase of glaucoma. Many therapeutic agents have been devised and discovered in the prior art for the treatment or amelioration of glaucoma and of the condition of increased intraocular pressure which precedes glaucoma. Other compounds known to be useful in treating intraocular pressure are disclosed in the following patents.

U.S. Pat. No. 3,467,756 describes anti-glaucoma and intraocular hypotensive compositions which contain in an ophthalmic vehicle 10,11-dihydro-5-(3-methylaminopropyl)-5,10-epoxy-11-hydroxy-5H-dibenzo[a,d]cycloheptene or related derivatives.

U.S. Pat. No. 4,197,301 describes ophthalmic compositions which contain 1-(4-amino-6,7-dimethoxy-2-quinazolinyl)-4-(2-furanylcarbonyl)piperazine, also known under the name "prazosin".

U.S. Pat. No. 4,565,821 describes a method of topically administering certain dopamine antagonists to reduce ocular hypertension and to treat glaucoma.

U.S. Pat. No. 4,886,815 describes a method for treating retinal edema by administration of dopaminergic antagonists to a patient suffering from such conditions.

U.S. Pat. No. 5,066,664 describes 2-hydroxy-2-alkylphenylamino)-oxazolines and thiazolines as anti-glaucoma and vasoconstrictive agents.

U.S. Pat. No. 5,091,528 describe 6 or 7-(2-imino-2-imidazolidine)-1,4-benzoxazines as adrenergic agents useful for treating glaucoma.

The foregoing and other anti-glaucoma and ocular hypotensive compounds and agents of the prior art do not provide such treatment or cure for glaucoma and ocular hypertension which is satisfactory in all respects. Therefore, the pharmacological and related arts and sciences continue searching for additional and better anti-glaucoma and ocular hypotensive agents.

1,2-bis(2-aminophenoxy)ethane-N,N,N',N'-tetraacetic acid (BAPTA) is a specific $Ca^{2+}$ chelator that has been used to clamp extracellular $Ca^{2+}$ to desired levels. On the other hand, the acetoxymethyl ester of BAPTA (BAPTA-AM) the uncharged esterified form of the parent compound is used to clamp intracellular $Ca^{2+}$($Ca^{2+}$i). BAPTA-AM penetrates biological cell membranes and is hydrolyzed by intracellular esterases yielding the original charged impermeable form of the compound once again capable of buffering/clamping $Ca^{2+}$. (This is reported in Molecular Probes: Handbook of Fluorescent Probes and Research Chemicals; Richard P. Haugland 1992–1994; Section 20: Calcium Indicators, Chelators and Ionophores, pages 119–128.)

SUMMARY OF THE INVENTION

Surprisingly it has been discovered in accordance with the present invention that calcium chelating agents are effective as anti-glaucoma agents and as agents for reducing intraocular pressure, when such agents are applied to the mammalian eye in a pharmaceutical composition, preferably in a topical ophthalmic composition. Accordingly, in one aspect the present invention relates to a method of treating glaucoma, or ocular hypertension by topically administering to the mammalian eye an ophthalmic composition which contain an effective amount of a calcium chelating agent. A preferred example of calcium chelating agents suitable as the active ingredients of the ophthalmic compositions of the invention are:

and esters, e.g. the lower alkyl and alkoxyalkyl esters thereof. Such esters may be represented by the general formula wherein R is lower alkyl, e.g. an alkyl radical having from 1 to 6 carbon atoms, or —$R^1$—O—C—$R^2$ wherein $R^1$ is a lower alkylene radical, e.g. an alkylene radical having from 1 to 6 carbon atoms, and $R^2$ is R, as defined above. R, $R^1$ and $R^2$ may be interrupted with O or N radicals as in alkyloxy alkyl and alkylaminoalkyl moieties, e.g. $R_1$ may be $—CH_2—N(CH_3)CH_2CH_2—$ and $—CH_2—O—CH_2—CH_2—$. Preferably, $R^1$ and $R^2$ will comprise from 1 to 4 carbon atoms, e.g. 1 carbon atom.

While not wishing to be bound by theory it is believed that calcium chelating agents, e.g. 1,2-bis (2-aminophenoxy) ethane-N, N, N', N'-tetraacetic acid (BAPTA) or the acetoxymethyl ester of BAPTA (BAPTA-AM), are useful for treating hypertensive glaucoma, because intracellular ($Ca^{2+}$i) is fundamental in the activation/control and modulation of epithelial fluid secretion. Thus, clamping/lowering the level of $Ca^{2+}$i in the ciliary epithelium, the tissue responsible for aqueous humor formation and a determinant of intraocular pressure (IOP), will reduce inflow and therefore IOP.

The ophthalmic compositions of the invention contain the active ingredient in a concentration range of approximately 0.0001 to 0.1 percent weight by volume. The composition itself includes, in addition to the active ingredient, such excipients which are per se well know in the art for preparing ophthalmic compositions, particularly ophthalmic solutions. In accordance with a method of the invention the ophthalmic compositions, preferably ophthalmic solutions, are applied topically to the mammalian eye approximately 1 or 2 times daily.

In another aspect, the present invention also relates to methods and compositions for delivering drugs to cells having acetylcholinesterase or acetylcholine receptors on their cell surfaces. The drugs preferably contain at least one carboxylic acid group, and are formulated as a prodrug, with the carboxylic acid group(s) neutralized by derivatization with an alkyl ester blocking group. Such prodrugs also comprise a di- ) or trimethyl ammonium moiety, an isobutyl or t-butyl moiety, or a sterically similar structure and are able to bind to acetylcholinesterase or an acetylcholine receptor.

As stated above, the prodrugs are designed to be liberated as a charged species once within the target cell through the action of intracellular esterases. While this aspect of the invention applies to any carboxylic acid-containing drug to be delivered to the cytoplasm of cells having cell surface acetylcholine-binding proteins, in a preferred example the prodrug comprises a calcium chelator compound as described above, together with at least one hydrophobic blocking group such as the acetoxymethyl ester (AM) blocking groups mentioned above. In a particularly preferred example, the calcium chelator prodrug comprises the non-polar BAPTA derivative BAPTA-AM; once inside the cell, esterases convert the uncharged BAPTA-AM to the polar calcium chelator BAPTA. The conversion of the prodrug to a polar form limits the tendency of neutral compounds to quickly leak out of the cell.

The method of this aspect of the invention involves providing the prodrug to cells such as neural cells (for example, ciliary epithelial and retinal cells) having cell surface acetylcholinesterase or acetylcholine receptors by joining the prodrug to a chemical structure mimicking the acetylcholine molecule. Hasan et al., *J. Biol. Chem.* 256:7781–7785 (1981), Hasan and Cohen, *J. Biol. Chem.* 255:3898–3904 (1980) and Cohen et al., *J. Biol. Chem.* 257:14087–14092 (1982), each of which is incorporated by reference herein as part of this specification, have shown in structural studies of inhibitors of acetylcholinesterase that a substantial determinant of acetylcholinesterase-substrate binding specificity is the trimethyl ammonium structure of acetylcholine. Analogs of acetylcholine that have groups sterically resembling this trimethyl ammonium structure, such as, without limitation, a dimethyl ammonium or t-butyl moiety, are also able to bind and activate acetylcholinesterase, demonstrating the relative importance of the tertiary structure of the acetylcholinesterase substrate over the positive charge of the acetylcholine.

Thus, the prodrugs of this aspect of the invention are joined to an acetylcholine ester or pseudo-acetylcholine ester (collectively referred to herein as a "pACE" moiety) that is able to bind acetylcholinesterase or an acetylcholine receptor; the pACE moiety may then be liberated from the prodrug by acetylcholinesterase-mediated hydrolysis, or the entire prodrug-pACE molecule may be transported through the plasma membrane. In either case the drug is then liberated within the cell through the action of cytoplasmic esterases.

DETAILED DESCRIPTION OF THE INVENTION

In one aspect of the invention the compounds which are utilized in accordance with the method of the present invention, and in the pharmaceutical compositions of the present invention, are calcium chelating agents. In this regard the term calcium chelating agent is defined as those compounds which complex with calcium ions under physiological conditions, e.g. in an aqueous media at a pH of from 6.5 to 7.8. Specific and preferred examples of calcium chelating agents which are utilized in accordance with the present invention are provided below.

Pharmaceutically acceptable salts of the calcium chelating agents can also be used in accordance with the present invention. A pharmaceutically acceptable salt is any salt which retains the activity of the parent compound and does not impart any deleterious or untoward effect on the subject to which it is administered and in the context in which it is administered.

Such a salt may be derived from any organic or inorganic acid or base. The salt may contain a mono or polyvalent ion. Of particular interest where the acid function is concerned are the inorganic ions, e.g. sodium, potassium, etc. Organic amine salts may be made with amines, particularly ammonium salts such as mono-, di- and trialkyl amines or ethanol amines. Salts may also be formed with caffeine, tromethamine and similar molecules. It is only important that the cation of any salt of a calcium chelating agent utilized in the compositions or methods of this invention be exchangeable with intracellular calcium ions.

For reducing intraocular pressure in a mammalian eye, and particularly for treatment of glaucoma in humans suffering from that condition, the active compounds (or mixtures or salts thereof) are administered in accordance with the present invention to the eye admixed with an ophthalmically acceptable carrier. Any suitable, e.g., conventional, ophthalmically acceptable carrier may be employed. A carrier is ophthalmically acceptable if it has substantially no long term or permanent detrimental effect on the eye to which it is administered. Examples of ophthalmically acceptable carriers include water (distilled or deionized water) saline and other aqueous media. In accordance with the invention, the active compounds are preferably soluble in the carrier which is employed for their administration, so that the active compounds are administered to the eye in the form of a solution. Alternatively, a suspension of the active compound or compounds (or salts thereof) in a suitable carrier may also be employed.

In accordance with the invention the active compounds (or mixtures or salts thereof) are administered in an ophthalmically acceptable carrier in sufficient concentration so as to deliver an effective amount of the active compound or compounds to the eye. Preferably, the ophthalmic, therapeutic solutions contain one or more of the active compounds in a concentration range of approximately 0.0001% to approximately 0.1% (weight by volume) and more preferably approximately 0.0005% to approximately 0.1% (weight by volume).

Any method of administering drugs directly to a mammalian eye may be employed to administer, in accordance with the present invention, the active compound or compounds to the eye to be treated. By the term "administering directly" is meant to exclude those general systemic drug administration modes, e.g., injection directly into the patient's blood vessels, oral administration and the like, which result in the compound or compounds being systemically available. The primary effect on the mammal resulting from the direct administering of the active compound or compounds to the mammal's eye is preferably a reduction in intraocular pressure. More preferably, the active useful compound or compounds are applied topically to the eye or are injected directly into the eye. Particularly useful results are obtained when the compound or compounds are applied topically to the eye in an ophthalmic solution (ocular drops).

Topical ophthalmic preparations, for example ocular drops, gels or creams, are preferred because of ease of application, ease of dose delivery, and fewer systemic side effects, such as cardiovascular hypotentions. An exemplary topical ophthalmic formulation is shown below in Table I. The abbreviation q.s. means a quantity sufficient to effect the result or to make volume.

TABLE I

| Ingredient | Amount (% W/V) |
| --- | --- |
| Active Compound in accordance with the invention, | about 0.0001 to about 0.1 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| antioxidant | as needed |
| Purified Water | as needed to make 100% |

Various preservatives may be used in the ophthalmic preparation described in Table I above. Preferred preservatives include, but are not limited to, benzalkonium chloride, stabilized chlorine dioxide, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particularly sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

The ophthalmic solution (ocular drops) may be administered to the mammalian eye as often as necessary to maintain an acceptable level of intraocular pressure in the eye. In other words, the ophthalmic solution (or other formulation) which contains the calcium chelating agent as the active ingredient, is administered to the mammalian eye as often as necessary to maintain the beneficial hypotensive effect of the active ingredient in the eye. Those skilled in the art will recognize that the frequency of administration depends on the precise nature of the active ingredient and its concentration in the ophthalmic formulation. Within these guidelines it is contemplated that the ophthalmic formulation of the present invention will be administered to the mammalian eye approximately once or twice daily.

With regard to the drug delivery aspect of the invention, the prodrug-pACE compounds described herein may be administered topically, as set forth above for the calcuim chelator drugs. In the embodiments of the present invention involving a prodrug-pACE moeity, the drug may be, but need not be, a drug for the treatment of glaucoma or another ocular condition. In some embodiments, the drug will be a therapeutic agent for delivery to other acetylcholinesterase or acetylcholine receptor-containing cells, such as brain, CNS, and sensory afferent cells, and cells of the neuromuscular junction. The prodrug-pACE molecules may be administered systemically, may be injected intramuscularly or intravenously, or provided in an infusion solution; in each case appropriate inactive carrier and tonicity ingredients are well known by those of skill in the art to provide a pharmacologically acceptable formulation. Preferably, the prodrug-pACE compounds are provided in a topical ophthalmic formulation.

The calcium chelating agents which are used as the active effective ingredients in the ophthalmic composition aspect of the present invention are described and shown below:

EXAMPLE 1

Figure 1:
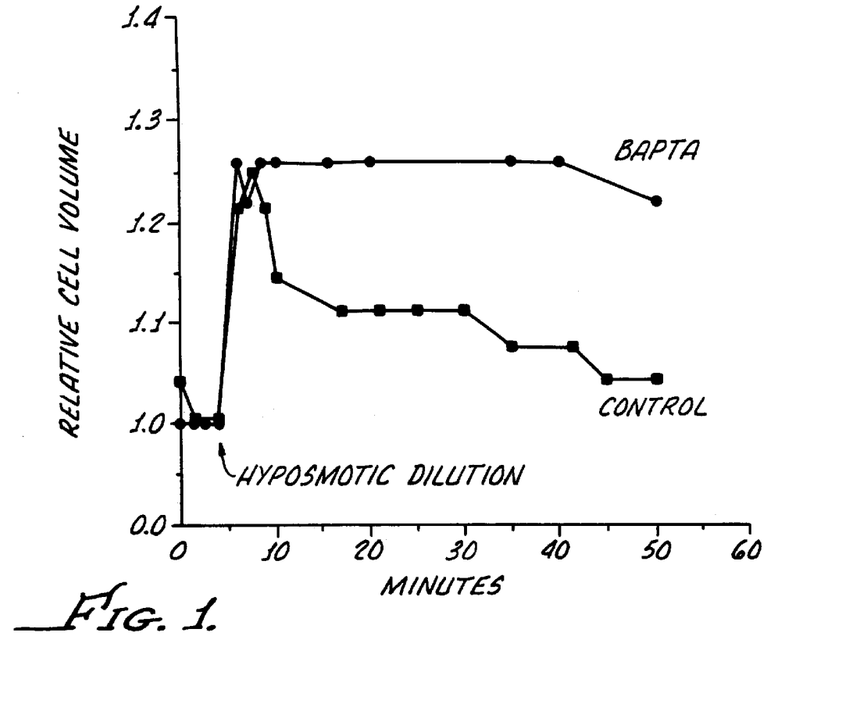
FIG. 1 is a graph showing the effect of topical administration of the drug BAPTA-AM on the regulatory volume decrease (RVD) of a suspension of cultured human non-pigmented ciliary epithelial cells.

This aspect of the present invention is demonstrated by in vitro and in vivo data. In FIG. 1, 20 M BAPTA-AM were found to totally depress the regulatory volume decrease (RVD) that occurs following hyposmotic swelling of cultured human non-pigmented ciliary epithelial (NPE) cells. In this example, NPE cells were loaded in an isosmotic (290 mOsm) solution containing 20 M BAPTA-AM for 30 minutes prior to suspension in a hyposmotoic (198 mOsm) solution. Control cells were subjected to the same hyposmotic solution but without prior loading with BAPTA. Changes in cell volume were measured using a Coulter Counter interfaced to a Coulter Channelyzer. It is noted that, following osmotic swelling, control cells regulate towards their original isosmotic volume while BAPTA-loaded cells remain swollen. The above findings indicate that intracellular BAPTA via chelation of $Ca^{2+}i$ inhibits solute and osmotically obliged $H_2O$ efflux. Because the $Ca^{2+}i$-dependent ion flux pathways activated following osmotic cell swelling of NPE cells are involved in aqueous secretion, BAPTA will inhibit aqueous humor formation and, thus, lower IOP.

Figure 2:
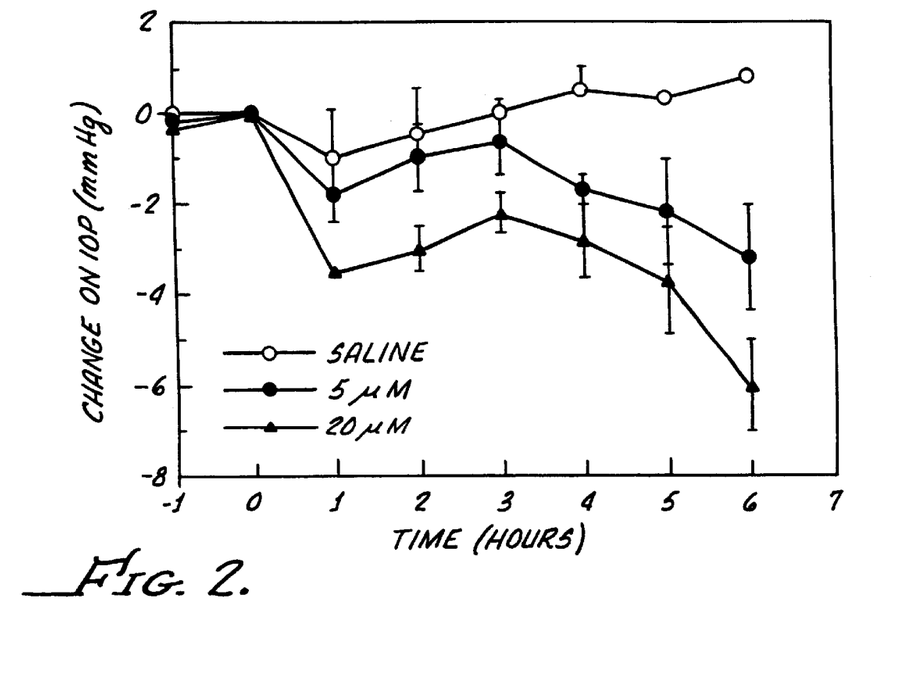
FIG. 2 is a graph showing the effect of intracameral administration of two dosages of the drug BAPTA-AM on the intraocular pressure (IOP) in the rabbit eye.
Figure 3:
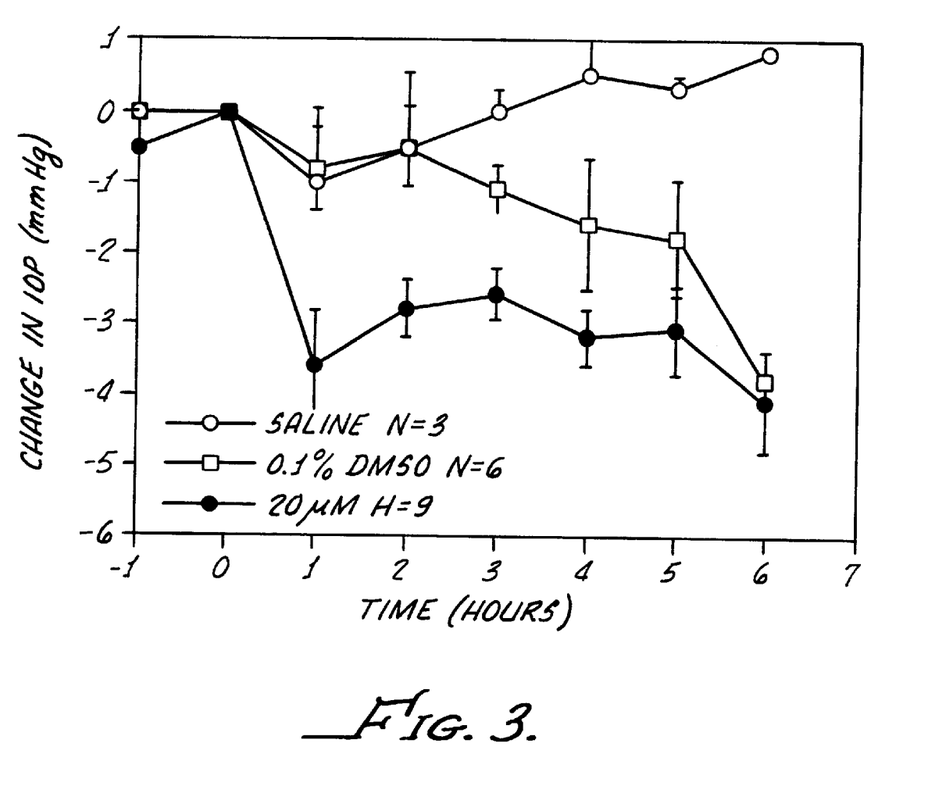
FIG. 3 is a graph showing the effect of intracameral administration of the drug BAPTA-AM, as compared to saline and dimethyl sulfoxide (DMSO) on the intraocular pressure (IOP) in the rabbit eye.

In the in vivo studies normotensive rabbits were injected intracamerally with 5 or 20 M BAPTA-AM. FIGS. 2 and 3 shows that 20 M BAPTA lowered IOP by 4 to 6 mm of Hg within 6 hours. Taken together the above in vitro and in vivo experiments demonstrate that chelation of $Ca^{2+}i$ in the ciliary epithelium will reduce IOP.

Several modifications of the present invention may become readily apparent to those skilled in the art in light of the present disclosure. For example, pACE (acetylcholine-like esters) derivatives of BAPTA or other carboxylic acid-containing calcium chelating agents will provide target-specific activity for lowering IOP. In general, since acetylchlorine esterases reside primarily in the ciliary body and retina, pACE derivatives of BAPTA or another calcium chelating agent should only be hydrolyzed in the above tissue/cell types when topically delivered to the eye.

The advantages of using pACE derivatives of BAPTA or another calcium chelating agent are as follows: First, $Ca^{2+}i$ will only be chelated/buffered in the ciliary epithelium and retina. Thus, other ocular cell types will be left unperturbed. Second, extracellular $Ca^{2+}$ which is critical for maintaining tight junction integrity in fluid transporting epithelia will remain unaltered since the acetylcholine ester of BAPTA will not be appreciably hydrolyzed in the absence of esterases. Third, since the retina including retinal ganglion cells will also contain BAPTA in its ionized form, large increases in retinal ganglion cell $Ca^{2+}i$ will be prevented. Because increases in retinal and in particular optic nerve $Ca^{2+}i$ are believed to play a deleterious role in the pathophysiology of glaucoma and neural degeneration, intracellular BAPTA in the above cell types will afford an additional neuroprotective effect.

In the drug delivery aspect of the invention, prodrug-pACE compounds and methods of delivering a carboxylic acid-containing drug within a cell having cell surface acetylcholine receptors or acetylcholinesterase, are intended to be within the scope thereof. Non-polar prodrugs are joined to a pACE; a group sterically similar to the trimethyl ammonium group of acetylcholine which is able to bind to acetylcholinesterase or an acetylcholine receptor. Such a pACE group may include, without limitation, a di- or trimethyl ammonium moiety or an isobutyl or t-butyl moiety. The prodrugs are liberated as a charged drug species by esterases once within the target cell; in a preferred example, the prodrug comprises the calcium chelator compounds described herein, however, the methods and compositions of this aspect of the invention are not limited to such compounds, and may be generally used for the delivery of drugs within the cytoplasm cells containing acetylcholine receptors or acetylcholinesterase.

The prodrug of the instant invention is preferably derivatized using a hydrophobic blocking group such as the acetoxymethyl ester (AM) blocking groups mentioned above. In a preferred example, a calcium chelator prodrug comprises the non-polar acetoxymethyl ester-derivatized BAPTA derivative BAPTA-AM; once inside the cell, esterases convert the uncharged BAPTA-AM to the polar calcium chelator BAPTA. The neutral prodrug is able to pass across the plasma membrane, whereupon the intracellular conversion of the prodrug to a polar form limits the tendency of the prodrug to quickly leak out of the cell.

The method of this aspect of the invention involves directing the prodrug to cells such as neural cells having cell surface acetylcholinesterase or acetylcholine receptors by joining the prodrug to a chemical structure mimicking the acetylcholine molecule. Analogs of acetylcholine having a t-butyl moiety in place of the trimethyl ammonium structure, as well as other analogous structures, are also able to bind and activate acetylcholinesterase, demonstrating the relative importance of the tertiary structure of the acetylcholinesterase substrate over the positive charge of the acetylcholine in receptor and acetylcholinesterase binding. The pACE moiety permits the binding of the prodrug-pACE compound to acetylcholinesterase with a Km or KD of between about 0.02 and about 15 mM, preferably between about 0.02 and about 5 mM, most preferably between about 0.02 and about 3 mM.

As discussed above, the prodrugs of this aspect of are joined to a pACE. The pACE moiety may then be liberated from the prodrug by acetylcholinesterase-mediated hydrolysis, or the entire prodrug-pACE molecule may be transported through the plasma membrane. While the invention is not limited hereby, in one aspect the structure of the prodrug-pACE molecule is as follows (hereinafter termed "Structure B"):

wherein
  r is 0–8 and DRUG is a drug optionally blocked with at least one alkoxy alkyl ester,
  R is selected from the group consisting of $(CH_3)_mCH_q(CH_2)_p-$ and $(CH_3)_mN(CH_2)_p-$,
  wherein
    m is 2 or 3,
    p is 0–8, and
    q is 3 minus m; and
  R' is selected from the group consisting of:
    a) $-(CH_2)_n-$,
      wherein
        n>1;
    b)

wherein the indeterminate bond is not in the ortho position, and
    c)

This structure will bind to acetylcholinesterase, but the spacer moiety prevents the prodrug-pACE from being cleaved by this enzyme. Once the prodrug-pACE crosses the plasma membrane, intracellular esterases (not having the same substrate specificity as acetylcholinesterse) will cleave the ester linkages, thereby simultaneously converting the prodrug to a charged carboxylic acid derivative, and releasing this charged drug within the cell.

In another example, the prodrug-pACE molecule has the following structure, hereinafter termed "Structure A":

wherein
  m is 0–8,
  DRUG is a drug optionally blocked with at least one alkoxy alkyl ester,
  Z is selected from the group consisting of $(CH_3)_mCH_q(CH_2)_p-$ and $(CH_3)_mN(CH_2)_p-$;
  X is selected from the group consisting of S or O;
  n>1; and
  R and R" are each independently selected from the group consisting of:
    H, and lower alkyl.

In this embodiment, the prodrug-pACE moiety first binds the acetylcholinesterase, which then cleaves the ester linkage proximal to the pACE moiety, yielding the carboxylic acid:

Upon decarboxylation, $CO_2$ is liberated to yield the uncharged species which is then able to pass through the cell membrane. Cytoplasmic esterases convert the prodrug to the polar carboxylic acid form of the drug:

HOOC-DRUG.

Prodrug-pACE compounds such as those described above can be made using standard organic synthetic methods.

EXAMPLE 2

A prodrug-pACE compound of the following structure is synthesized using standard synthetic methods.

This compound comprises the calcium chelator BAPTA blocked with three acetoxymethyl ester (AM) moieties, and containing a single N-linked pACE group in place. The compound is dissolved in an ophthalmically acceptable carrier for topical delivery to the eye. As indicated above, such prodrug-pACE compounds are specifically targeted to cilliary epithelial and retinal cells, without substantially affecting other cell types. In the above formulation, based on Formula B, the compound will bind acetylcholine receptors and cell surface acetylcholinesterase without being hydrolyzed thereby. The electronically neutral prodrug is then transported or permitted to penetrate the cell membrane, where cytoplasmic esterases convert the prodrug-pACE into the tetraacetic acid form of BAPTA capable of modulating the intracellular concentration of free $Ca^{++}$, thereby providing a neuroprotective function.

The compound is instilled into the eye of a mammal suffering high intraocular pressure. The prodrug-pACE compound passes through the cornea and the drug is concentrated within ciliary epithelial and retinal ganglion cells. Monitoring of intraocular pressure following treatment reveals that intraocular pressure is significantly lower than was the case prior to treatment.

Drug compounds in addition to the calcium chelating agents specifically described herein are included within this aspect of the invention, so long as they contain at least one carboxylic acid group. In view of the above, it is clear that the scope of the present invention should be interpreted solely on the basis of the following claims, as such claims are read in light of the entire disclosure.

What is claimed is:

1. A therapeutic composition comprising: an apolar prodrug comprising a structure represented by the formula:

wherein r is 0–8 and DRUG is a drug optionally blocked with at least one alkoxy alkyl
wherein r is 0–8 and DRUG is a drug optionally blocked with at least one alkoxy alkyl ester,
R is selected from the group consisting of $(CH_3)_mCH_q(CH_2)_p$— and $(CH_3)_mN(CH_2)_p$—,
wherein
  m is 2 or 3,
  p is 0–8, and
  q is 3 minus m; and
R' is selected from the group consisting of:
  a) —$(CH_2)_n$—,
   wherein
    n>1;
  b)

wherein the indeterminate bond is not in the ortho position, and
  c)

2. The therapeutic composition of claim 1 wherein said polar active drug has calcium chelating activity.

3. The therapeutic composition of claim 2 wherein said polar active drug has the structure represented by the formula:

and lower alkyl and alkoxyalkyl esters thereof.

4. The apolar prodrug of claim 2 wherein R is selected from the group consisting of:

a) $(CH_3)_3C(CH_2)_2$—,
b) $(CH_3)_2N(CH_2)_2$—,
c) $(CH_3)_3N^+(CH_2)_2$—; and
R' consists of $(CH2)2$—;
r is 1;
and said DRUG comprises a compound of the formula:

where each X is independently an alkoxy alkyl ester.

5. The apolar prodrug of claim 4 wherein R is $(CH_3)_3C(CH_2)_2$— and at least one X is an acetoxymethyl ester.

6. The apolar prodrug of claim 4 wherein R is $(CH_3)_3N^+(CH_2)_2$— and at least one X is an acetoxymethyl ester.

7. The apolar prodrug of claim 4 wherein R is $(CH_3)_2N(CH_2)_2$— and at least one X is an acetoxymethyl ester.

8. A therapeutic composition comprising an apolar prodrug comprising a structure having the formula:

wherein
m is 0–8;
DRUG is a drug optionally blocked with at least one alkoxy alkyl ester;
Z is selected from the group consisting of $(CH_3)_mCH_q(CH_2)_p$— and $(CH_3)_mN(CH_2)_p$—;
X is selected from the group consisting of S or O;
n>1; and
R and R' are each independently selected from the group consisting of H, and lower alkyl.

9. The apolar prodrug of claim 6 represented by the structure:

10. The prodrug of claim 7 wherein Z is (CH₃)₃C—.

11. The prodrug of claim 7 wherein Z is (CH₃)₃N⁺—.

12. The prodrug of claim 7 wherein Z is (CH₃)₂N—.

* * * * *

UNITED STATES PATENT AND TRADEMARK OFFICE
CERTIFICATE OF CORRECTION

PATENT NO. : 6,350,780 B1
DATED : February 26, 2002
INVENTOR(S) : Garst et al.

It is certified that error appears in the above-identified patent and that said Letters Patent is hereby corrected as shown below:

Column 2,
Line 67, delete "-$R^1$-O-C-$R^2$" and insert in place thereof $$---R^1-O-\overset{\overset{\displaystyle O}{\|}}{C}-R^2---$$

Signed and Sealed this

Twenty-sixth Day of November, 2002

Attest:

Attesting Officer

JAMES E. ROGAN
Director of the United States Patent and Trademark Office